(12) United States Patent
Bhawalkar et al.

(10) Patent No.: US 10,413,361 B2
(45) Date of Patent: Sep. 17, 2019

(54) DEVICE AND METHOD FOR SKIN TREATMENT

(71) Applicant: Candela Corporation, Wayland, MA (US)

(72) Inventors: Jayant Bhawalkar, Auburndale, MA (US); Kevin Schomacker, Maynard, MA (US)

(73) Assignee: Candela Corporation, Wayland, MA (US)

(*) Notice: Subject to any disclaimer, the term of this patent is extended or adjusted under 35 U.S.C. 154(b) by 95 days.

(21) Appl. No.: 15/488,571

(22) Filed: Apr. 17, 2017

(65) Prior Publication Data

US 2018/0296269 A1   Oct. 18, 2018

(51) Int. Cl.
| | |
|---|---|
| A61B 18/20 | (2006.01) |
| G02B 27/10 | (2006.01) |
| G02B 27/42 | (2006.01) |
| G02B 27/09 | (2006.01) |
| G02B 5/00 | (2006.01) |
| A61B 18/22 | (2006.01) |
| A61N 5/06 | (2006.01) |
| A61B 18/00 | (2006.01) |

(52) U.S. Cl.
CPC ............ *A61B 18/203* (2013.01); *A61B 18/20* (2013.01); *A61B 18/22* (2013.01); *A61N 5/0616* (2013.01); *G02B 5/001* (2013.01); *G02B 27/0927* (2013.01); *G02B 27/0944* (2013.01); *G02B 27/0955* (2013.01); *G02B 27/1086* (2013.01); *G02B 27/4205* (2013.01); *G02B 27/4277* (2013.01); *A61B 2018/0047* (2013.01); *A61B 2018/00452* (2013.01); *A61B 2018/2035* (2013.01); *A61B 2018/20554* (2017.05); *A61B 2018/205545* (2017.05); *A61B 2018/2261* (2013.01); *A61B 2018/2294* (2013.01)

(58) Field of Classification Search
CPC .................. A61B 18/20; A61B 18/203; A61B 2018/2035; A61B 2018/2266; A61B 2018/2294; A61B 2018/00315; A61B 2018/00432; A61B 2018/0047; A61N 5/06; A61N 5/0613; A61N 5/0616; A61N 2005/0632; A61N 2005/0642
USPC .......... 606/9, 10–13, 16–19; 607/88–91, 93; 128/898

See application file for complete search history.

(56) References Cited

U.S. PATENT DOCUMENTS

| | | | |
|---|---|---|---|
| 7,072,045 B2 | 7/2006 | Chen et al. | |
| 8,289,603 B2* | 10/2012 | DeBenedictis | ........ G02B 5/001 359/204.1 |
| 8,915,907 B2 | 12/2014 | Suckewer | |
| 9,247,995 B2 | 2/2016 | Suckewer | |
| 9,259,594 B2* | 2/2016 | Wang | ................... A61N 5/0613 |

(Continued)

*Primary Examiner* — Ahmed M Farah
(74) *Attorney, Agent, or Firm* — Manelli Selter PLLC; Edward Stemberger

(57) ABSTRACT

A device and a method for fractional skin treatment. The device employs two diffractive optical elements. One of the diffractive optical elements provides two coaxial laser beams and another diffractive optical element splits the two coaxial laser beams into a plurality of beamlets. A lens arranged to receive the plurality of the laser beams and to focus them in a skin treatment plane. The lens forms an image where each of the beamlets is imaged as a spot with a high intensity central area and a lower intensity area surrounding the central area.

9 Claims, 3 Drawing Sheets

(56) References Cited

U.S. PATENT DOCUMENTS

| | | | |
|---|---|---|---|
| 9,326,748 B2 | 5/2016 | Sumi | |
| 2015/0025599 A1* | 1/2015 | Bornstein | A61N 5/0613 607/88 |
| 2019/0099220 A1* | 4/2019 | Eisenmann | A61B 18/203 |

* cited by examiner

DEVICE AND METHOD FOR SKIN TREATMENT

The present apparatus and method relate to methods and apparatuses for treatment of biological tissues such as dermatological tissue. In particular, the present invention is directed towards skin rejuvenation including facial rejuvenation by reducing the appearance of wrinkles and fine lines, pigmented age-spots, pigment, and blemish removal.

BACKGROUND

Fractional skin treatment is a relatively new skin treatment technique. The treatment is performed by application to the skin of a plurality of focused laser beams. The beams are organized into one or two dimensional arrays. The plurality of laser beams affects a corresponding number of skin locations and forms microscopic columns of treated skin spots or areas. The treated skin areas are surrounded by untreated skin areas. The treated skin areas that could be micro-lesions are scattered over the skin and support a faster skin healing than if the entire area was treated. Fractional skin treatment has certain benefits over conventional laser skin treatment and the approach is gaining popularity in the market.

Different types of beam splitters are used to generate a plurality of laser beams from a single laser beam. One of the types of beam splitters is a Diffractive Beam Splitter. Diffractive optical element (DOE) and in particular diffractive beam splitters are periodic phase structures that split the input laser beam into multiple diffractive orders or beamlets, while retaining the divergence angle, diameter and polarization of the input beam.

These beamlets are characterized by an equal intensity and equal angle to one another. There are both one-dimensional and two-dimensional (1D/2D) diffractive beam splitting elements. 1D elements split beams along a straight line whereas 2D elements produce beams arranged in a matrix of, for example, 2×2 or 6×6 spots.

Usually, a lens is placed after such element as a diffractive beam splitter and the focused array or matrix of laser spots will appear in the focal plane of the lens. The distance or pitch between the spots in the focal plane depends on the working distance of the lens and the separation angle that is determined during the design of the DOE.

The following US patents and patent application Publications describe different uses of DOE for dermatological skin treatments: U.S. Pat. Nos. 7,072,045; 8,289,603; 8,915,907; 9,247,995; 9,259,594; 9,326,748.

The columns of injury induced by the fractional laser treatment can range from gentle photothermal or photochemical events designed to change one or more functions in tissue, to more intense photothermal events coagulating and or ablating cones of tissue causing a wound healing response with the goal of promoting neocollagenesis and neoelastogenesis. Strongly focused picosecond pulses can also lead to subsurface coagulative or ablative zones inducing a wound healing response without damaging the protective outer skin layers. Both neocollagenesis and neoelastogenesis leads to an improvement in the appearance of wrinkles and fine lines commonly known as rhytides. Fractional laser treatments with diffractive beamsplitters are well verse for generating finite zones of injuries promoting neocollagenesis and neoelastogenesis.

LIST OF FIGURES AND THEIR BRIEF DESCRIPTION

SUMMARY

A device and a method for fractional skin treatment. The device employs two diffractive optical elements. One of the diffractive optical elements (DOE) such as an axicon, provides two coaxial laser beams. One of the laser beams has a ring cross section and the other coaxial laser beam has a cross section with homogenous energy distribution. Another diffractive optical element such as a beamsplitter, splits the two coaxial laser beams into a plurality of beamlets. Each beamlet is also a coaxial beam having a ring shaped energy distribution beam and a beam with a homogenous energy distribution. A lens arranged to receive the plurality of the laser beams and to focus them in a skin treatment plane. The lens forms an image where each of the beamlets is imaged as a spot with a high intensity central area and a lower intensity area surrounding the central area.

DESCRIPTION

Although the highly focused fractional beams are well verse for generating zones of injuries promoting neocollagenesis and neoelastogenesis improving wrinkles and rhytides, these highly focused beams are less adept for treating pigmentation as focused array of beams have poor tissue coverage. The use of an axicon diffractive optic helps to improve tissue coverage allowing better coverage of pigmentation. Combining an axicon diffractive optic with a diffractive beamsplitter allows both higher tissue coverage of pigmentation by the lower fluence rings formed by the axicon and lower tissue coverage or higher fluence focused core beams for treating wrinkles and rhytides. The combination of the two diffractive optics allows the relative amounts going to the rings and core beam to vary based on the design of the optics.

Figure 1:
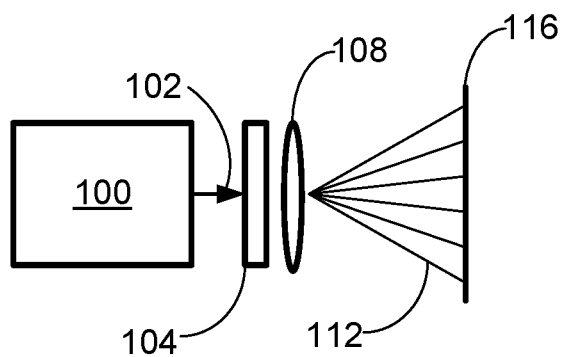
FIG. 1 is an example of a known device typically used for fractional skin treatment.

FIG. 1 demonstrates a known apparatus typically used for fractional skin treatment. The apparatus includes a single mode laser 100 emitting a single transversal mode ($TEM_{00}$) laser beam 102, a beam splitter 104 configured to split laser beam 102 into a plurality of beamlets 112, for example forming a pattern of 6×6 or 10×10 laser beamlets. The beam splitter could be a diffractive optical element (DOE) such as a diffractive beam splitter. A lens 108 focuses beamlets 112 forming in image plane 116 a 6×6 dots matrix. The image plane could be a surface of skin or tissue. Such devices are well designed for fractional skin treatment.

Figure 2:
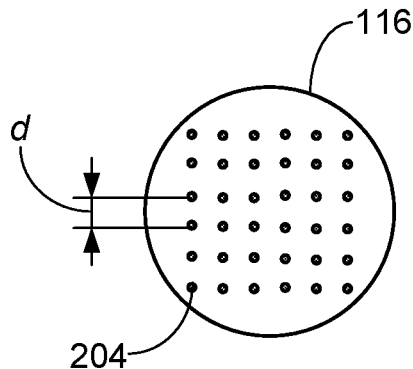
FIG. 2 is an example of an image of a 6×6 matrix of laser spots produced by device of FIG. 1.

FIG. 2 is an example of an image of a 6×6 matrix of laser spots produced by lens 108 in image plane 116. Each of the skin treatment laser spots 204 is a focused laser spot. The diffractive beamsplitter can be designed to have a specific separation angle which defines based on the focusing optic the distance between each beamlets. The inter-spot distance d is typically larger than the size of focused laser spot 204 with typical distances between 0.2 mm and 1.0 mm Depending on the inter-spot distance, the focused laser spots 204 cover less than 5% of image plane 116. Although such device is well designed for skin rejuvenation, it is less than perfect for clearing pigmented age-spots due to the fact that the highly focused beams have by design low tissue coverage, typically less than 5%.

Figure 3:
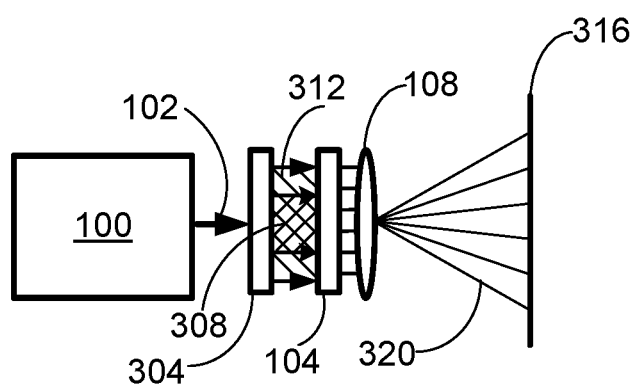
FIG. 3 is an example of the present device for fractional skin treatment.
Figure 4:
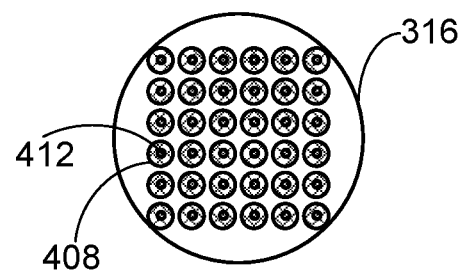
FIG. 4 is an example of an image of a 6×6 matrix of laser spots produced by the present device.

To improve tissue coverage, while also having highly focused beams, the present disclosure suggests to combine two diffractive optical elements (FIG. 3): the first diffractive optical element could be an axicon 304 and a second diffractive optical element could be a beam splitter 104. The diffractive axicon 304 transforms distribution of energy of incident laser beam 102 into a ring-shaped laser beam 312 containing for example 50% of the incident laser beam intensity and a central laser beam 308 also containing 50% of laser intensity. The ring-shaped laser beam 308 and the central laser beam 312 are coaxial beams.

Figure 3A:
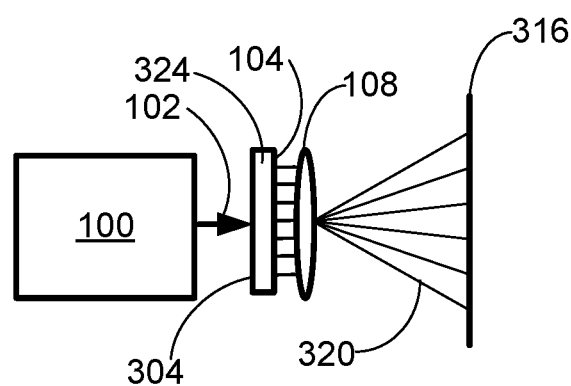
FIG. 3A is an example of the present device for fractional skin treatment with two diffractive optic elements formed on a common optic substrate.

Alternatively to the two separate diffractive optic elements, a diffractive element could be manufactured or formed on a common optic substrate as a single diffractive optic element. For example, the beamsplitter feature 104 could be patterned onto one face of the common optic substrate (FIG. 3A) and axicon features 304 could be patterned onto the other face of the common optic substrate. This allows for the use of a single diffractive optic element 324 followed by a focusing lens to generate the desired array of highly focused central spots 412 with a ring of energy surrounding each of the central spots.

Generally the axicon could be configured to meet different skin treatment requirements and provide different relative percentage or ratio of laser intensity between coupled into ring shaped laser beam 312 and central laser beam 308. For example, the ratio could vary to be 10% to 90%, 40% to 60% or 80% to 20%. Typically, the ratio is set by the design of the axicon. The first diffractive optical element (axicon) 304 could also be designed to support different divergence of ring shaped laser beam 312 and central laser beam 308 and thus control the diameter of either one of the rings 408 formed by the ring-shaped laser beam 312 and central spot 412 formed by central beams 308. In addition, the diffractive axicon can be designed to have a specific separation angle which defines based on the focusing optic the diameter of the ring-shaped beam. Typical diameters would range between 0.2 mm to 0.5 mm.

The ability to change the separation angle of the diffractive beamsplitter, the separation angle of the axicon, the relative percent energy split into the ring-shaped beam and central laser beam, the grid array (5×5, 5×10, 10×10, etc.) and the focus length on the focusing optics allows enough degrees of freedom to define the laser fluence of the central spot, the laser fluence of the ring-shaped beam, the inter-spot distance and hence the treatment area, and percent coverage of the treatment area. Typical treatment areas may range between 5 mm×5 mm to 25 mm×25 mm in size. Rectangular treatment areas are also possible by selecting as an example a 5×10 grid array, or different separation angles for the x and y axis of the 2D diffractive optic.

Lens 108 is arranged to receive the at least two laser beams and to focus the at least two laser beams onto an image plane 316 (skin treatment plane). This forms in image plane 316 an image of the central laser beam 412 surrounded by an image of a ring shape beam 408. Image plane 316 could be used to treat skin or tissue. Image of ring-shaped beam 408 could have a lower laser fluence as compared to the fluence of highly focused laser spots 412. Laser beams images 408 and 412 are focused laser spots. The centers of laser beam images 408 and 412 are located on the same grid points. Such a device allows in a single treatment, both low fluence toning procedures for pigmented skin with high tissue coverage and low tissue coverage laser induced optical breakdown (LIOB) for promoting collagen, elastin, and mucins regrowth and improving wrinkles, texture, and pores.

The described above device and method could be used for aesthetic skin treatments and in particular for fractional skin rejuvenation, which is a growing field of skin treatment.

It should be noted, however, that other and additional combinations of skin treatment energy using combined laser energy could be used to for skin treatment. These other combined laser energy beams are within the scope of the present disclosure and the claims.

What is claimed is:

1. A device for treating biological tissue, comprising:
   a laser configured to provide a laser beam;
   a first diffractive optical element configured to receive the laser beam and transform distribution of energy in the laser beam to a central spot and a surrounding ring of energy;
   a second diffractive optical element configured to receive the laser beam with transformed distribution of energy and to split it into at least two laser beams; and
   a lens arranged to receive the at least two laser beams and to focus the at least two laser beams and in a skin treatment plane,
   wherein a separation angle of the first diffractive optical element supports diameter of a ring-shaped beam of 0.2 mm to 0.5 mm; and
   wherein a separation angle of the second diffractive optical element is designed to set inter-spot distance between beamlets of 0.2 mm to 1 mm.

2. The device of claim 1, wherein the laser provides a single transversal mode ($TEM_{00}$) laser beam.

3. The device of claim 1, wherein the first diffractive optical element is a diffractive axicon.

4. The device of claim 1, wherein the first diffractive optical element transforms distribution of energy of incident laser beam into a ring-shaped laser beam and a central laser beam.

5. The device of claim 4, wherein the ring-shaped laser beam and the central laser beam are coaxial beams.

6. The device of claim 4, wherein a different ratio of laser intensity is coupled into the ring shaped laser beam and the central laser beam and wherein the ratio is a variable ratio.

7. The device for skin treatment of claim 4, wherein a lens forms in an image plane an image of the ring-shaped beam surrounded by an image of a central laser beam.

8. The device of claim 1, wherein centers of the image of a ring-shaped beam surrounded by an image of a central laser beam are located on a same grid points.

9. The device of claim 1, wherein the second diffractive optical element is a diffractive beam splitter.

* * * * *